(12) United States Patent
Sarphie et al.

(10) Patent No.: US 11,435,341 B2
(45) Date of Patent: Sep. 6, 2022

(54) MONITORING CANCER RECURRENCE AND PROGRESSION

(71) Applicant: SEROXO LIMITED, Richmond (GB)

(72) Inventors: David Sarphie, Oxford (GB); Rubina Mian, Harborne Birmingham (GB)

(73) Assignee: SEROXO LIMITED, Richmond (GB)

( * ) Notice: Subject to any disclaimer, the term of this patent is extended or adjusted under 35 U.S.C. 154(b) by 473 days.

(21) Appl. No.: 16/337,035

(22) PCT Filed: Oct. 2, 2017

(86) PCT No.: PCT/GB2017/052947
§ 371 (c)(1),
(2) Date: Mar. 27, 2019

(87) PCT Pub. No.: WO2018/060741
PCT Pub. Date: Apr. 5, 2018

(65) Prior Publication Data
US 2020/0033327 A1 Jan. 30, 2020

(30) Foreign Application Priority Data
Sep. 30, 2016 (GB) ...................... 1616640

(51) Int. Cl.
*G01N 33/50* (2006.01)
*G01N 33/574* (2006.01)
(52) U.S. Cl.
CPC ..... *G01N 33/5094* (2013.01); *G01N 33/5038* (2013.01); *G01N 33/5091* (2013.01); *G01N 33/57434* (2013.01); *G01N 2800/52* (2013.01); *G01N 2800/56* (2013.01)

(58) Field of Classification Search
CPC ........... G01N 33/5094; G01N 33/5038; G01N 33/5091; G01N 33/57434; G01N 2800/52; G01N 2800/56
See application file for complete search history.

(56) References Cited

U.S. PATENT DOCUMENTS

| 6,159,683 | A | 12/2000 | Romaschin |
| 7,838,262 | B2 | 11/2010 | Mian et al. |
| 2005/0176061 | A1 | 8/2005 | Rosen |

(Continued)

FOREIGN PATENT DOCUMENTS

| JP | 2008514925 A | 5/2008 |
| WO | 2008/074131 | 6/2008 |

OTHER PUBLICATIONS

Lyman et al., "Incidence and Predictors of Low Dose-Intensity in Adjuvant Breast Cancer Chemotherapy: A Nationwide Study of Community Practices", J. Clin. Oncol. (2003) vol. 21, No. 24, 4524-4531.

(Continued)

*Primary Examiner* — Jennifer Wecker
*Assistant Examiner* — Michael Paul Shimek
(74) *Attorney, Agent, or Firm* — Duane Morris LLP

(57) ABSTRACT

The present invention provides rapid and simple methods of testing on whole blood samples for alerting cancer recurrence and assessing cancer progression relying on determination of the functionality of leucocytes (predominately neutrophils) to exhibit challenge-induced superoxide anion production with quantification by chemiluminescent measurement.

9 Claims, 1 Drawing Sheet

(56) References Cited

U.S. PATENT DOCUMENTS

| | | | |
|---|---|---|---|
| 2006/0014235 A1* | 1/2006 | Mian | G01N 33/5091 |
| | | | 435/25 |
| 2006/0194220 A1 | 8/2006 | Reddy | |
| 2010/0028932 A1 | 2/2010 | Loibner | |
| 2011/0223623 A1* | 9/2011 | Serrero | G01N 33/57423 |
| | | | 435/7.92 |
| 2013/0072844 A1 | 3/2013 | Granot | |
| 2014/0127179 A1 | 5/2014 | Thornthwaite | |

OTHER PUBLICATIONS

Crawford et al., "Chemotherapy-Induced Neutropenia, Risks, Consequences, and New Directions for Its Management", Cancer (2004) vol. 100, No. 2, 228-237.

Silber et al., "First-cycle blood counts and subsequent neutropenia, dose reduction, or delay in early-stage breast cancer therapy", J. Clin. Oncol. (1998) vol. 16, No. 7, 2392-2400.

Hu et al., "Intracellular Free Calcium Regulates the Onset of the Respiratory Burst of Human Neutrophils Activated by Phorbol Myristate Acetate", Cell Signal (1999) vol. 11, No. 5, 335-360.

Kaffenberger, W. et al., "The Respiratory Burst of Neutrophils, a Prognostic Parameter in Head and Neck Cancer?" Clinical Immunology and Immunopathology, vol. 64, No. 1, Jul. 1992, pp. 57-62.

Trulson, Agneta et al., "Lucigenin-Enhanced Chemiluminescence in Blood is Increased in Cancer" American Journal of Clinical Pathology, vol. 91, Issue 4, Apr. 1, 1989, pp. 441-445.

Shkapova, E.A. et al., "Lucigenin- and Luminol-Dependent Chemiluminescence of Blood Neutrophils in Patients with Renal Cancer" Bulletin of Experimental Biology and Medicine, vol. 149, No. 2, Aug. 2010, p. 239-241.

Schepetkin, I.A. et al., "Decreased luminol-dependent chemiluminescence response of neutrophils to recombinant human tumour necrosis factor in patients with gastric cancer" J. Cancer Res. Clin Oncol., 1991;117(2), pp. 172-174.

Lejeune, Marylene et al., "Prolonged but reversible neutrophil dysfunctions differentially sensitive to granulocyte colony-stimulating factor in children with acute lymphoblastic leukaemia" British Journal of Haematology, 1998, 102, pp. 1284-1291.

Rodrigues, George et al., "Pre-treatment risk stratification of prostate cancer patients: A critical review" Can Urol Assoc J., Apr. 2012, vol. 6, Issue 2, pp. 121-127.

International Search Report dated Dec. 1, 2017 for corresponding PCT/GB2017/052947.

Zivkovic, Morana, et al. "Oxidative burst of neutrophils against melanoma B16-F10." *Cancer Letters* 246.1-2 (2007): 100-108.

* cited by examiner

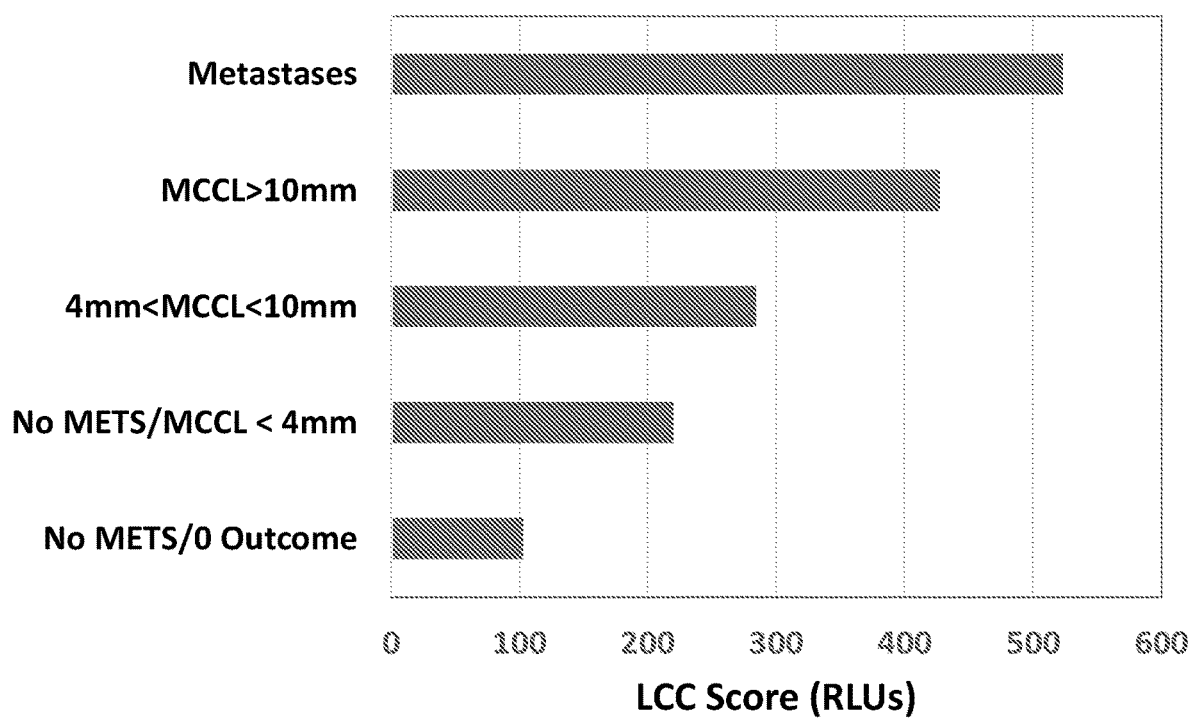

MONITORING CANCER RECURRENCE AND PROGRESSION

CROSS-REFERENCE TO RELATED APPLICATIONS

This application is a U.S. national phase application filed under 35 U.S.C. § 371 of International Application No. PCT/GB2017/052947, which was filed Oct. 2, 2017, and which claims the benefit of the filing date of GB 1616640.7, which was filed Sep. 30, 2016. The entire content of these applications is hereby incorporated by reference herein.

FIELD OF THE INVENTION

The present invention relates to in vitro methods for predicting cancer recurrence and monitoring cancer progression and treatment in individuals. More particularly, methods are provided which rely on determination of the functionality of leucocytes (predominately neutrophils) to exhibit challenge-induced superoxide anion production, i.e. produce a "respiratory burst" in response to in vitro activation. While such activation of leucocytes is known and is often referred to as leucocyte coping capacity (LCC), the invention provides new application in the field of cancer diagnosis which can for example be used to simply and quickly assess cancer status using whole blood samples without any need for fractionation. The invention has for example been shown to enable quick and convenient ranking of prostate cancer patients on the basis of tumour size and to enable distinction of such patients with metastases from patients with no metastases and relatively low tumour volume.

Such methodology may be applied prior to cancer treatment or after a period of cancer treatment to assess the effectiveness of the therapy. It may provide quick and convenient guidance for moderating therapeutic interventions, for example the time interval between chemotherapy sessions, change of drug dosage or change of form of treatment.

BACKGROUND TO THE INVENTION

Current techniques for monitoring cancer progression often use total blood counts, such as Total Leukocyte Count (TLC) or Absolute Neutrophil Count (ANC). These give the numbers of leukocytes or neutrophils, respectively per volume of blood. While they provide total numbers of specific cells, they tell the practitioner nothing of the functionality of the cells. Furthermore, these tests must be done in a hospital, health care clinic or other professional health care setting and are not suitable as self-tests.

Chemotherapy is known to cause a reduction in the population of circulating neutrophils (a condition known as neutropenia) by destroying rapidly-dividing cells in the bone marrow that produce neutrophils. Indeed, neutropenia is the major dose-limiting toxicity of chemotherapy and the primary driver of the dose delays and reductions that result in low relative dose intensity (RDI) (Lyman et al. (2003) J. Clin. Oncol. 21, 4524-4531.) Neutropenia is associated with the risk of life-threatening infections as well as chemotherapy dose reductions and delays that may compromise treatment outcomes (Crawford et al. (2004) Cancer 100, 228-237). Furthermore, researchers have clearly identified a need for improved methods of ranking early-stage breast cancer patients so as to make their therapy more efficient and reduce delays due to neutropenia (Silber et al. (1998) Cancer, J. Clin. Oncol. 16, 2392-2400).

It has now been surprisingly found that a simple whole blood test can be used to gain a rapid quantitative measure of cancer status either to guide treatment or provide insight into cancer recurrence relying on determination of challenge-induced superoxide production by leucocytes as discussed above. Such a test protocol has the additional advantage that it may be applied without change during cancer treatment to assess neutrophil function and provide warning of undesirable neutropenia.

Chemical inducers such as phorbol myristate acetate (PMA) are well-known for activating neutrophils in peripheral blood samples whereby retained capacity for superoxide production can be quantified as a measure of neutrophil functionality (Hu et al. Cell Signal (1999) 11, 335-360). Such use with whole blood samples with measurement of superoxide production by chemiluminescence to obtain an LCC score forms the basis of a test commercialised by Oxford MediStress Limited to quantify psychological stress in humans and animals; see European Patent no. 1558929 and related patents deriving from published International Application WO2004/042395. However, the data reported herein provides for the first time evidence for very different utility of the same type of blood test in cancer diagnosis. Of especial interest is that such a test has been shown to be capable of application to blood samples from prostate cancer patients whereby LLC score can be correlated with disease progression or continued remission; See Example 2. Such a ranking or stratification method is considered to be equally applicable to other cancers, especially for example breast cancers.

SUMMARY OF THE INVENTION

As indicated above, the invention relies on assessing the capacity of neutrophils, or preferably the total leucocyte component of whole blood, to produce superoxide in response to appropriate in vitro chemical challenge. Such quantified response with whole blood samples is commonly referred to as the leucocyte coping capacity (LCC) score. However, since this will largely be determined by neutrophil capability for such external stimulation to produce reactive oxygen species (ROS), reference may alternatively be made to the individual's neutrophil functionality level. Individuals with a higher neutrophil functionality level will have a greater potential superoxide production and, physiologically, will have greater neutrophil function.

In its broadest aspect, the present invention thus provides a method of assessing in a subject the neutrophil functionality level as an indicator of the presence of a tumour or other cancer, including cancer recurrence after a period of treatment, which comprises:
 (a) contacting a test sample comprising neutrophils obtained from said subject with an inducer capable of stimulating superoxide production in neutrophils under conditions suitable for such stimulation;
 (b) determining the increase of superoxide production above basal in said test sample after a time period to obtain a first result and
 (c) comparing said first result with a second comparator result,
whereby the presence of a tumour or other cancer, or a lack of a tumour or other cancer capable of affecting neutrophil function, in said subject is determined.

Commonly, where superoxide production is determined after a short period of inducer challenge by conventional chemiluminescence measurement, e.g. employing luminol and a portable luminometer, the basal chemiluminescence will be invariably so low in samples as not to require consideration. Thus, in these circumstances, total measured relative light units (RLUs) may be equated with induced superoxide production and as directly proportional to neutrophil functionality. This has been established to apply for example when using freeze-dried PMA/luminol reagent as supplied by Oxford MediStress for LCC scoring of whole blood samples and incubating the sample for 10 minutes at 37.5° C. in accordance with the standard protocol for use of that reagent. In other words, "determining the increase of superoxide production above basal" in the test sample may be equated with simple one step quantification of superoxide present at the end of the neutrophil stimulation period, e.g. 10-30 minutes after addition of the inducer.

Determining the presence of a tumour or other cancer may preferably extend to determination of ranking or status of the tumour or other cancer in terms of size and/or one or more other clinical indicators of degree of progression, including metastases. Thus, the second comparator result may be a pre-determined threshold recognised to equate with a particular cancer stratification status, e.g. size or metastases, for samples from patients with a known type of cancer.

Without wishing to be bound by theory, the effectiveness of the method may be related to cancers acting as an immunologically-active moiety.

It will be recognised that the second comparator result may correspond to induced superoxide production in a control sample from a different subject of the same species known to be healthy, e.g. a healthy human, ideally in a relaxed situation prior to sample provision. It may be a sample taken from the same individual after a period of cancer treatment and known to be in remission. Samples taken from individuals for the purpose of the present invention will be taken such that differential effects of psychological stress between the test sample and any comparator sample are minimized.

In an embodiment of the invention, a method of the invention as above may be applied to a plurality of samples from patients expected to have various degrees of progression of a particular cancer type, including possible remission after treatment, and comparison of results of quantification of induced superoxide production, preferably LCC score, used to assign each sample to a rank by correlation with one or more criteria indicative of disease progression, e.g. expected metastases and no metastases. Such a stratification method using a plurality of samples from prostate cancer patients is illustrated by Example 2. Such stratification will provide pre-determined thresholds which may be employed as a second comparator result in applying a method of the invention to further samples from patients suspected or known to have the same cancer to determine cancer status or to check for recurrence of such cancer after effective treatment.

The samples employed for a method of the invention will preferably be whole blood samples in which case as indicated above superoxide production will strictly equate more generally with leucocyte capacity for superoxide production (or alternatively stated ability to produce a respiratory burst). Such methodology importantly avoids centrifugation, which is known to affect cell reactivity, and also plating out of cells on glass slides which may also affect functionality. Blood samples as small as about 10-30 µl will suffice obtained using a conventional finger lancing device.

As already noted above, superoxide production may be conveniently measured by known simple chemiluminescence measurement using, for example, luminol or iso-luminol. Suitable protocols are disclosed for example in European Patent no. 1558929 of Oxford MediStress. Generally, an incubation temperature of 37-37.5° C. will be chosen and incubation continued for a pre-determined time, preferably consistent with maximal or near maximal chemiluminescence measurement. As referred to above, the freeze-dried composition comprising PMA and luminol salt as supplied by Oxford MediStress for LCC testing enables suitable test results from a finger prick of whole blood to be attained in just 10 minutes and was used for the tests reported in Example 2 as a preferred reagent.

While a conventional luminometer may be employed for detection of the chemiluminescence, such light detectors require expensive and fragile photomultipler tubes. Hence, use of an alternative photon detector may be preferred. In particular, a silicon photomultipler (Si-PM) may, for example, be favoured. Such a photon detector is deemed more robust for the purpose and to combine greater cost-effectiveness with sufficient sensitivity of photon detection. A suitable hand-held luminometer is available again from Oxford MediStress as part of the CopingCapacity™ test kit, which also provides freeze—dried PMA/luminol—containing reagent composition as noted above.

If need be or desired, the measured superoxide production above basal for each sample may be corrected by reference to the number of leucocytes or neutrophils in the sample. Since as indicated above, neutrophils can be expected to be responsible for the majority of superoxide production above basal, residual capacity of leucocytes above basal for in vitro-induced induction can be termed "neutrophil functionality level" and will be so referred to hereinafter.

BRIEF DESCRIPTION OF THE FIGURE

FIG. 1 illustrates use of LCC scores to stratify prostate cancer patients with reference to maximum cancer core length (MCCL) and presence or absence of metastases.

DETAILED DESCRIPTION

Methods of the invention are of especial interest in monitoring cancer progression in human cancer patients or for providing an indicator of cancer recurrence following treatment of such patients but it will be appreciated also have application to cancer treatment in the veterinary field, especially in relation to other mammals.

As noted above, a method of the invention for assessing in a subject the presence of a tumour or other cancer comprises steps which may equally be applied to assess the effect of cancer treatment on neutrophil functionality level of a cancer patient during the treatment:
  (i) contacting a test sample, preferably a whole blood sample, comprising neutrophils obtained from the patient with an inducer capable of stimulating superoxide production in neutrophils under conditions suitable for such stimulation;
  (ii) determining the increase of superoxide production above basal in said test sample after a time period to obtain a first result and
  (iii) comparing said first result with a second control result,
whereby reduction in induced increase in superoxide production in said test sample compared with the control result is indicative of depressive effect of the treatment on neutrophil functionality level.

It will be appreciated that the control result may be derived from a sample taken from the same patient at an earlier time point prior to or during said treatment.

Steps (i) to (iii) may be repeated thereby providing a highly convenient means for long-term ("longitudinal") monitoring of the effect of cancer treatment on the patient's physiological status. Such methodology is envisaged as a convenient means for example for aiding decision-making by clinicians in applying chemotherapy and/or radiotherapy for cancer treatment, for example the time interval between chemotherapy and/or radiotherapy sessions which will be founded on clinically relevant cell function rather than just counting cells or looking at structure.

Hence, importantly the invention enables a single combination of kit components to be provided for both cancer diagnosis and ranking and for monitoring in the same patient undesirable depletion of neutrophil function during cancer treatment.

In another preferred embodiment, the invention provides a method of assessing the neutrophil functionality level in a subject post-cancer treatment as an indicator of change of physiological status associated with cancer recurrence which comprises:

(a) contacting a test sample, preferably a whole blood sample, comprising neutrophils obtained from said subject with an inducer capable of stimulating superoxide production in neutrophils under conditions suitable for such stimulation;

(b) determining the increase of superoxide production above basal in said test sample after a time period;

(c) comparing the increase in superoxide production above basal in said test sample with the increase in superoxide production above basal in a second comparator sample at the same time point and under the same conditions, said second comparator sample being a sample taken at an earlier time point post-cancer treatment and while the subject is considered in cancer remission, wherein increased induced superoxide production in said test sample compared with in said second comparator sample is indicative of cancer recurrence.

Thus, the methodology of the invention can be envisaged as enabling all of the following in relation to cancer management and treatment:

1. Leukocyte test as a predictor of cancer aggression and reoccurrence.
2. Leukocyte test as an objective marker of the effectiveness of therapies.
3. Use of a leukocyte test as an end point for therapies.
4. Leukocyte test for balancing and moderating therapeutic interventions (for example the time interval between chemotherapy sessions, and radiotherapy sessions) optimising cell function (rather than just counting cells or looking at structure).
5. Leukocyte test as a controlled checkpoint during therapies
6. Leukocyte test as a sensor of the micro environment during cancer therapy
7. Leukocyte test to optimise therapeutic intervention during cancer Other potential uses and some potential benefits which are now of note are:

Can be used for early detection of cancers.

Can be used as a home monitor to determine optimal responses.

Lifestyle (food, exercise, relaxation techniques) can be adjusted to determine optimal response (personalised optimal outcomes).

Can aid the bespoke treatment of cancers (personalised medicine); for example, but not exclusively optimising traditional medicine with alternative therapies.

Can be used to combine alternative medicinal approaches (e.g. dietary with traditional approaches).

Holistic treatment of cancers (lifestyle, traditional and alternative regimes) can be combined and optimised.

Home monitoring can be conducted on a regular basis to monitor, optimise and follow effectiveness of treatments.

Can serve as an early warning for recurrence following remission.

Simple, easy to use—results obtainable in 10 minutes, minimally invasive.

Unit for protocol can be portable, not lab-based thereby minimising cost.

First technique to allow integration of treatments (traditional, alternative, lifestyle) based on objective assessment of clinically relevant neutrophil functionality.

Facilitates truly personalised objective cancer care.

It is envisaged that methods of the invention are widely applicable to a variety of cancers such as breast cancer, ovarian cancer and other cancer types. Such methods may find especial application in relation to for example prostate cancer.

Of particular relevance to convenience of use as noted above is that there is no necessity to fractionate blood samples to obtain an isolated leucocycte or neutrophil fraction. Blood samples for carrying out a method of the invention may be directly contacted with any chemical inducer capable of stimulating superoxide production in neutrophils. The inducer may be preferably phorbol myristate acetate (PMA), more particularly for example the microbial product phorbol 12-myristate 13-acetate obtainable from Sigma. However alternative inducers which might be employed are well-known. They include N-formyl-Met-Leu-Phe (fLMP chemotactic peptide), zymosan, lipopolysaccharide and adrenaline. The chemical inducer may be conveniently stored in the form of a freeze-dried reagent composition, e.g. as a pellet, for dissolution in an appropriate buffer solution, e.g. phosphate-buffered saline.

For additional convenience coupled with high sensitivity, as indicated above, superoxide production will be linked to chemiluminescence signal measurement using a suitable amplifier such as luminol or iso-luminol (see EP 1558929 and Hu et al. (1999) Cell Signal 11, 355-360). Luminol or iso-luminol may be conveniently supplied with the chemical inducer in a single reagent composition for addition to samples as exemplified by the commercially-available freeze-dried composition comprising PMA and luminol noted above. For each sample, chemiluminescence in the presence of added inducer may be measured using a conventional portable luminometer at a suitable time point. However as indicated above use of an alternative more advanced photon detector may be preferred, for example, especially a silicon photomultiplier.

In a further aspect of the invention, there is provided a system for carrying out a method as discussed above comprising a light detector such as a portable luminometer or Si-PM and system for analysing the results to provide an alert for a neutrophil functionality level associated with risk of cancer or a cancer status, e.g. metastatic cancer. The same system may also be employed in monitoring cancer treatment as discussed above and provide additionally alert for low neutrophil function favouring desirability of changing or stopping cancer treatment.

As noted above, it has now been shown that steps (a) to (c) of a method of the invention as set out above for detecting the presence of a cancer if applied to a plurality of samples from patients with various degrees of progression of a particular cancer type, including possibly remission after treatment, will provide results which can be used to rank each cancer patient by correlation with one or more criteria indicative of disease progression. For example, such criteria may be one or more tumour size ranges, e.g. a range of maximum cancer core length (MCCL), metastases and no metastases. In this way LLC scores can be used to stratify cancers to evaluate disease severity. Application of such analysis to whole blood samples from prostate cancer patients has for example established that LCC scores for samples from patients with metastatic prostate cancer are significantly higher than for whole blood samples from patients in remission or with low grade non-metastatic prostate cancer as equated with a MCCL of less than 4 mm. Such cancer status ranking can be predicted to be equally applicable to other tumour types, e.g. breast cancer, and to enable determination of LCC score thresholds to be used in determining tumour progression or recurrence.

Thus, in a preferred embodiment of the invention, there is provided a method of assessing cancer status in a subject suspected or known to have a tumour, or a subject previously known to be in tumour remission, which comprises:
(a) contacting a test sample comprising neutrophils obtained from said subject, preferably a whole blood sample, with an inducer capable of stimulating superoxide production in neutrophils under conditions suitable for such stimulation;
(b) determining the increase of superoxide production above basal in said test sample after a time period to obtain a first result and
(c) comparing said first result with a second comparator result which is a pre-determined threshold which correlates with one or more criteria equating with a cancer status, e.g. a size range and/or metastases, whereby cancer status is determined.

The cancer status may be assessed as no tumour, e.g. continued remission. It may equate with presence of a tumour complying with one or more criteria defining a degree of tumour progression, e.g. progression to metastases. Such a method may be especially preferred for rapid assessment of whether a tumour such as a prostate or breast cancer tumour has advanced to metastases or not.

The following non-limiting examples illustrate the invention.

EXAMPLES

Example 1: Example of Protocol for Use of PMA Challenge to Assess Neutrophil Functionality Level in Whole Blood Samples To measure the background blood chemiluminescence level, 10 μl of whole blood is transferred into a silicon anti-reflective tube. 90 μl of $10^{-4}$M luminol (5-amino-2,3-dihydrophalazine; Sigma) diluted in phosphate buffer is added. The tube is then shaken gently. To measure chemiluminescence produced in response to PMA challenge, 20 μl of PMA (Sigma) at a concentration of $10^{-3}$M is added. For each tube, chemiluminescence may be measured for 30 secs every 5 mins in a luminometer, for a total of 30 mins. When not in the luminometer, tubes are incubated at 37.5° C., e.g. in a dry block heater.

A single reading after incubation at 37.5° C. for 10 minutes may be found convenient and more preferable.

It will be appreciated that the same challenge test may be carried out with any sufficiently sensitive photon detector, e.g. a Si-PM may be employed Example 2: Stratification of Prostate Cancer Patients Using LCC Scores The study was approved by a local ethics committee and conducted at an NHS teaching hospital in London. 70 men with biochemical failure following radical prostate radiotherapy prior to salvage therapy were recruited to the study. After consenting to the study and prior to undergoing whole-body multi-parametric MRI (WB-MRI), finger prick samples of blood (10 microlitres) were obtained from each patient in triplicate and analysed for neutrophil functionality level using freeze-dried PMA/luminol reagent composition as commercially available from Oxford MediStress for LCC scoring. This involved mixing the blood with a buffered solution (100 microlitres) of reagents containing the freeze-dried PMA/luminol mixture. After incubation in a dry block heater for 10 minutes at 37.5° C., the sample was evaluated for production of reactive oxygen species, measured using a portable luminometer (3M Clean Trace™. One set of samples (in triplicate) was obtained from each test subject.

The test results were analysed by grouping test subjects into various categories according to disease severity ("disease significance"). Categories were:
No Metastases, Recurrence Unlikely
No Metastases, Maximum Cancer Core Length (MCCL) <4 mm
MCCL between 4 mm and 10 mm
MCCL>10 mm
Metastases Scores for neutrophil functionality level for each patient in these categories were averaged (mean) and these averages plotted on a bar chart as shown in FIG. 1

Results:
The data shows strong correlation between LCC score and increasing disease severity.
17/18 patients with LCC scores>450 had significant disease equating with MCCL>4 or metastases.
Statistically significant difference (via t-test) was shown between samples from patients with metastases and samples from the patient group with no or low grade cancer (no metastases/no recurrence or MCCL<4).

These results for the first time demonstrate that neutrophil functionality level as assessed by LCC score measured using the Oxford MediStress system can be used to stratify tumours with reference to criteria for progression status and point to especial interest for example in using LCC scores as a means for rapidly distinguishing advanced prostate cancer with likelihood of metastases, from no or low grade cancer.

We claim:
1. A method of detecting increased levels of superoxide production above basal in a test sample from a subject suspected or known to have cancer, or a subject previously known to be in cancer remission, said method comprising:
(a) contacting a test whole blood sample obtained from said subject with phorbol myristate acetate (PMA) and luminol;
(b) after a selected time period, measuring a chemiluminescence resulting from step (a);

(c) wherein an increased chemiluminescence is the measured chemiluminescence in step (b) and is higher than a basal chemiluminescence level measured from contacting with PMA and luminol a control whole blood sample obtained from a subject who does not have cancer, wherein said measured chemiluminescence correlates with one or more criteria equating with a cancer status, whereby cancer status is determined;

said one or more criteria being selected from no tumor, a tumor size range, metastases or no metastases; and wherein the increased chemiluminescence above the basal chemiluminescence level is associated with progression of cancer ranking on the basis of tumor size or progression to metastases.

2. A method as claimed in claim 1 wherein the cancer is prostate cancer.

3. A method as claimed in claim 2 wherein said cancer is distinguished as advanced to metastases or no metastases.

4. A system configured to carry out a method according to claim 1 comprising a photon detector for quantitative measurement of chemiluminescence and an analysis component configured to compare the difference of the measured chemiluminescence levels and provide an alert for a neutrophil functionality level associated with a cancer status of interest selected from no tumour, a tumour size range, metastases or no metastases.

5. A system as claimed in claim 4 wherein said photon detector is a portable luminometer.

6. A method as claimed in claim 1 wherein chemiluminescence is measured using a portable luminometer.

7. The system of claim 4, wherein the alert for a neutrophil functionality level associated with a cancer status of interest selected from no tumor, a tumor size range, metastases or no metastases is conditioned on the degree of the measured chemiluminescence difference.

8. The method of claim 1, wherein the subject is distinguished as having a condition selected from: with cancer without metastasis, with cancer with metastasis, or with cancer of a selected tumor size.

9. The method of claim 1, wherein the selected time period is 10 minutes.

* * * * *